United States Patent
Freeman

(10) Patent No.: US 11,013,443 B2
(45) Date of Patent: May 25, 2021

(54) EMERGENCY PEDIATRIC ECG LEAD SET WITH INTEGRATED INSTRUCTIONS

(75) Inventor: Curtis Freeman, Windham, NH (US)

(73) Assignee: Koninklijke Philips N.V., Eindhoven (NL)

( * ) Notice: Subject to any disclaimer, the term of this patent is extended or adjusted under 35 U.S.C. 154(b) by 2175 days.

(21) Appl. No.: 13/806,338

(22) PCT Filed: Jun. 2, 2011

(86) PCT No.: PCT/IB2011/052429
§ 371 (c)(1),
(2), (4) Date: Apr. 2, 2013

(87) PCT Pub. No.: WO2012/001553
PCT Pub. Date: Jan. 5, 2012

(65) Prior Publication Data
US 2013/0211210 A1   Aug. 15, 2013

Related U.S. Application Data

(60) Provisional application No. 61/359,665, filed on Jun. 29, 2010.

(51) Int. Cl.
*A61B 5/259* (2021.01)
*A61B 5/107* (2006.01)
(Continued)

(52) U.S. Cl.
CPC ............ *A61B 5/259* (2021.01); *A61B 5/1072* (2013.01); *A61B 5/303* (2021.01); *A61B 5/4836* (2013.01);
(Continued)

(58) Field of Classification Search
CPC . A61B 5/1072; A61B 5/04087; A61B 5/4836; A61B 5/259; A61B 5/303;
(Continued)

(56) References Cited

U.S. PATENT DOCUMENTS 4,713,888 A * 12/1987 Broselow ............. A61B 5/1072
33/512
5,356,428 A * 10/1994 Way ..................... A61B 5/0408
600/385

(Continued)

OTHER PUBLICATIONS

Definition of Disposed. Merriam-Webster Dictionary, retrieved on Dec. 21, 2015; Retrieved from the Internet: <http://www.merriam-webster.com/dictionary/disposed>.*

(Continued)

*Primary Examiner* — Gary Jackson
*Assistant Examiner* — Sebastian X Lukjan

(57) ABSTRACT

A cardiac electrotherapy device is described having an electrode lead set (100) and an instruction placard (140) having a set of medical guidance instructions (210) integrated with the electrode lead wire (160). The medical guidance instructions are printed on an elongated readable surface which is attached along its long edge to the electrode lead wire. The invention is particularly useful during cardiac emergencies involving pediatric or infant patients, whose medical dosage limits may be closely correlated with patient length.

20 Claims, 8 Drawing Sheets

(51) Int. Cl.
 A61N 1/04 (2006.01)
 A61B 5/30 (2021.01)
 A61B 5/00 (2006.01)
 A61B 90/00 (2016.01)

(52) U.S. Cl.
 CPC ........... *A61N 1/046* (2013.01); *A61N 1/0496* (2013.01); *A61B 2090/061* (2016.02); *A61B 2562/222* (2013.01)

(58) Field of Classification Search
 CPC ........ A61B 2562/222; A61B 2090/061; A61N 1/0496; A61N 1/3925; A61N 1/39–3993; A61N 1/362; A61N 1/046; A61N 1/3904; A61N 1/39044; A61N 1/39046; A61N 1/3906; A61N 1/3912; A61N 1/3918; A61N 1/3931; A61N 1/3937; A61N 1/3943; A61N 1/395; A61N 1/3956; A61N 1/3962
 USPC .................. 600/301, 374; 606/142; 607/4–5
 See application file for complete search history.

(56) References Cited

U.S. PATENT DOCUMENTS

| | | | | |
|---|---|---|---|---|
| 5,626,618 | A * | 5/1997 | Ward | A61N 1/0517 607/124 |
| 6,134,468 | A | 10/2000 | Morgan et al. | |
| 7,558,610 | B1 * | 7/2009 | Odderson | A61B 5/04001 600/384 |
| 9,072,444 | B2 | 7/2015 | Burnes et al. | |
| 2003/0088239 | A1 * | 5/2003 | Takaki | A61B 5/04087 606/1 |
| 2003/0195567 | A1 | 10/2003 | Jayne et al. | |
| 2005/0085736 | A1 | 4/2005 | Ambrose et al. | |
| 2005/0148898 | A1 * | 7/2005 | Odderson | A61B 5/04001 600/544 |
| 2006/0206152 | A1 | 9/2006 | Covey et al. | |
| 2007/0100288 | A1 | 5/2007 | Bozeman et al. | |
| 2008/0086817 | A1 | 4/2008 | Zucker et al. | |
| 2009/0126743 | A1 * | 5/2009 | Wingert | A61F 13/471 128/898 |

OTHER PUBLICATIONS

Definition of hydrogel. Merriam-Webster Dictionary, retrieved on Dec. 21, 2015; Retrieved from the Internet: <http://www.merriam-webster.com/dictionary/hydrogel>.*

Definition of integral. Merriam-Webster Dictionary, retrieved on Dec. 21, 2015; Retrieved from the Internet: <http://www.merriam-webster.com/dictionary/along>.*

Definition of integral. Merriam-Webster Dictionary, retrieved on Dec. 21, 2015; Retrieved from the Internet: <http://www.merriam-webster.com/dictionary/integral>.*

Broselow; Pediatric Resuscitation System Medical Equipment Emergency Pdediatric Resuscitation; Armstrong Medical Industries, Inc.; Downloaded: http://www.armstrongmedical.com/index.cfm/go/product.detail/sec/3/ssec/14/fam/15026; Jan. 2010 10:11:53; p. 1.

Common Cents EMS Supply-E . . . PDF(Chapter 9. Pedi Slide Chart) Downloaded: http://www.savelives.com/cgi-bin/instock.pl?group=9&subgroup=8; Jan. 26, 2010. pp. 1-5.

* cited by examiner

11 KG.
Epi. 11mL (ET)
Bicarb. 11-22mEq
CaCl 3.3mL
Atrop. .11-.33mg (ET)
Defib. 22 Joules
Lid. 1.1mg. (ET)
Narcan .11mg.
ET Size 4.0mm 10 KG.
Epi. 10mL (ET)
Bicarb. 10-20mEq
CaCl 3.0mL
Atrop. .1-.3mg (ET)
Defib. 20 Joules
Lid. 10mg. (ET)
Narcan .10mg.
ET Size 3.5mm actual dosages given child measured 9 KG.
Epi. .09mL (ET)
Bicarb. 9-18mEq
CaCl 2.7mL
Atrop. .09-.27mg (ET)
Defib. 18 Joules
Lid. 9mg. (ET)
Narcan .09mg.
ET Size 3.5mm 8 KG.
Epi. .08mL (ET)
Bicarb. 8-16mEq
CaCl 2.4mL
Atrop. .08-.24mg (ET)
Defib. 16 Joules
Lid. 8mg. (ET)
Narcan .08mg.
ET Size 3.5mm 7 KG.
Epi. .07mL (ET)
Bicarb. 7-14mEq
CaCl 2.1mL
Atrop. .07-.21mg (ET)
Defib. 14 Joules
Lid. 7mg. (ET)
Narcan .07mg.
ET Size 3.0mm 6 KG.
Epi. 0.6mL (ET)
Bicarb. 6-12mEq
CaCl 1.8mL
Atrop. .06-.18mg (ET)
Defib. 12 Joules
Lid. 6mg. (ET)
Narcan .06mg.
ET Size 3.0mm

EMERGENCY PEDIATRIC ECG LEAD SET WITH INTEGRATED INSTRUCTIONS

Aspects of this invention relate generally to cardiac rescue systems for treating adults and infants. More specifically, the present invention integrates a "Broselow"-type pediatric tape with defibrillator electrodes to enable a more effective and accurate rescue apparatus.

The invention is particularly applicable to defibrillator/monitors that are to be used by medical personnel trained in Advanced Cardiac Life Support. It also applies to the ECG Lead sets used on bedside monitors that are used within the hospital Emergency Room or Pediatric Intensive Care Units.

Sudden cardiac death is the leading cause of death in the United States. Most sudden cardiac death is caused by ventricular fibrillation ("VF"), in which the muscle fibers of the heart contract without coordination, thereby interrupting normal blood flow to the body. The only known treatment for VF is electrical defibrillation, in which an electrical pulse is applied to a patient's heart. The electrical shock clears the heart of the abnormal electrical activity (in a process called "defibrillation") by depolarizing a critical mass of myocardial cells to allow spontaneous organized myocardial depolarization to resume.

A defibrillator is the most commonly treatment for VF. Defibrillators may analyze ECG signals from the heart and, upon detection of a treatable arrhythmia, send electrical pulses to a patient's heart through electrodes applied to the torso to defibrillate the patient or to provide for external pacing of the patient's heart. The electrical pulse must be delivered within a short time after onset of VF in order for the patient to have any reasonable chance of survival.

Treatment of VF in pediatric and infant patients presents particular difficulties. First, VF in the pediatric and infant patient population requires somewhat different treatment, particularly in therapeutic dose levels, than adults. Second, VF is so rare in this population that most trained rescuers are not familiar with the appropriate dosing levels. Pediatric dosing refers to, for example, lower defibrillating energies, different rates of CPR compressions and breathing, and pharmaceutical therapy. A typical cardiac rescue in a pediatric patient may involve all of these treatments.

There are tools available for guiding the proper pharmaceutical treatment in children and infants. For example, the Broselow pediatric emergency tape is known in the art as a measuring device for quickly assessing the size and weight of a child or infant, and for providing instructions as to appropriate medical treatment for various-sized children. One example of the Broselow tape is described in U.S. Pat. No. 4,713,888 entitled "Measuring Tape for Directly Determining Physical Treatment and Physiological Values", by Broselow. FIG. 1 illustrates the tape 10 in use on a pediatric patient 20.

The Broselow Pediatric Emergency Tape 10 is a piece of laminated paper designed to aid Emergency Medical Technicians, paramedics, nurses, and other medical personnel with proper medication dosage and equipment sizing for pediatric emergencies. The tape 10 uses a color-coding system, called the Broselow-Luten Color Coding System (B-LPS) to differentiate between various classes of equipment and medications, with each color corresponding to the patient's approximate weight class. In this manner, emergency personnel can quickly identify what is needed to save a pediatric patient's life.

FIGS. 1 and 2 illustrate how the Broselow tape is used. When a pediatric patient 20 is brought into the treatment location, the tape is extended along the patient's length. At one end of the tape is an index mark 30, which the rescuer aligns with the top of the patient's head. The tape portion that is adjacent to the patient's feet has medical guidance instruction 40, which is appropriate for a patient having that length. Of course, the patient's length serves as a correlator to its weight. The instruction 40 contains guidance for proper dosage for that particular pediatric weight.

A disadvantage of the Broselow Pediatric Emergency Tape is that it is not often used, but is a separate piece of equipment that must be stored and readily available in an emergency. Having the tape readily available in any emergency greatly assists in providing appropriate treatment in an often-times stressful situation.

The inventors recognize that an ECG is also one of the most basic patient measurements. Thus, a set of cardiac therapy electrodes would be deployed in almost every instance that the Broselow Tape would be of use. In the field a defibrillator/monitor is commonly used by paramedics. An electrode set 50, as illustrated in FIG. 3, is included with each defibrillator/monitor. Each electrode set 50 includes at least two electrode pads, each connected to the defibrillator monitor via lead wires 60. Some electrode sets, such as the M3870A Infant/Child Pediatric FR2 Reduced-Energy Defibrillator Pads, manufactured by Philips North America, Andover, Mass., are designed to be used exclusively on pediatric patients.

Accordingly, it is an object of the present invention to simplify cardiac emergencies involving pediatric patients, by integrating pediatric-specific medical guidance instructions into a cardiac rescue device electrode set. The invention reduces the amount of clutter during rescues, reduces the need for storage space between rescues, and enables quicker and more accurate treatment for pediatric patients.

Another object of the present invention is to describe a method for rescue of cardiac pediatric patients, comprising steps of deploying a defibrillator electrode set which has indicia on the lead wire for estimating the pediatric patient's characteristics. The indicia further have therapeutic dosage instructions specific to that patient's characteristics. The characteristic may include length, weight, and/or age.

In the drawings:

FIGS. 2A and 2B illustrate prior art embodiments of a Broselow Tape having medical guidance instructions.

Figure 4:
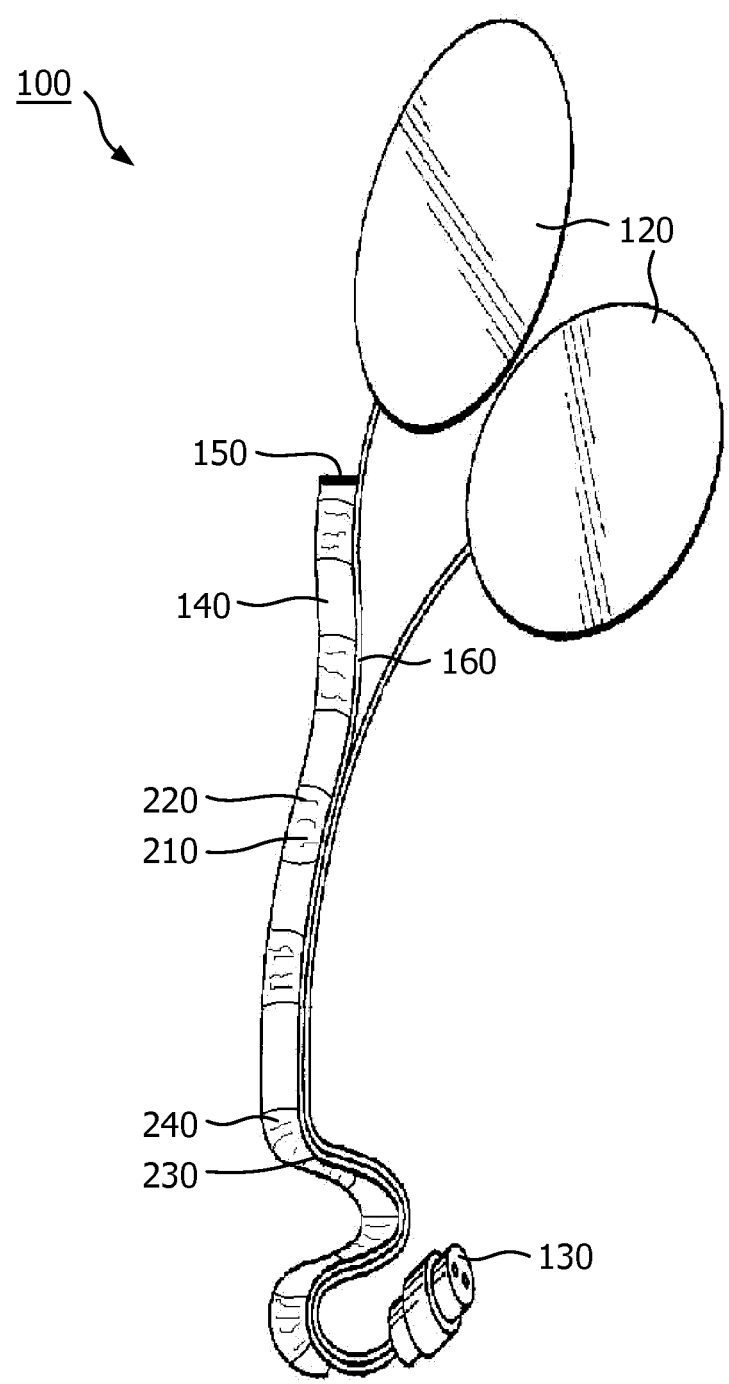
FIG. 4 illustrates a preferred embodiment of the present invention; a combination of the Broselow Tape with an electrode set for use in cardiac rescue emergencies involving pediatric and infant patients.

Turning now to FIG. 4, there shown is an electrode lead set 100 for a cardiac treatment device, such as a defibrillator or an ECG monitor, which integrates an instruction placard 140 with the lead set 100. The electrode lead set 100 includes one or more adhesive skin electrodes 120 which, when adhesively applied to a patient's skin, conduct defibrillation current to the patient. The lead set 100 further includes a connector 130 for connecting the lead set 100 to the cardiac treatment device.

A lead wire 160 connects each of the electrodes 120 to a corresponding pin in the connector 130. The lead wire is preferably long enough to accommodate use on various sizes of patients without being so long as to interfere with other aspects of the rescue. Preferably, the lead wire is three to four feet in length, and is covered by a polymeric insulation material.

The instruction placard is an elongated flap of flexible material that is attached along its length to a lead wire. The placard may be constructed of a durable plastic or coated paper which is adhered to or bonded to the lead wire. Alternatively, the placard may be an integral part of the lead wire insulation material and thus may be formed at the same time as the insulation. Alternatively, the insulation itself may constitute the instruction placard, without the use of attached flap material.

The instruction placard 140 has indicia imprinted thereon which are used to guide a rescuer in the assessment and treatment of pediatric and infant patients. The indicia include an index mark 150 which is preferably located at one end of the placard. Along the length of the instruction placard 140 are location zones 220. Each location zone 220 correlates to a particular patient characteristic, the characteristic dependent upon the distance that the zone 220 is from the index mark 150. Each location zone 220 may be color-coded with a unique or distinctive color to simply provide zone identification during the rescue.

Figure 1:
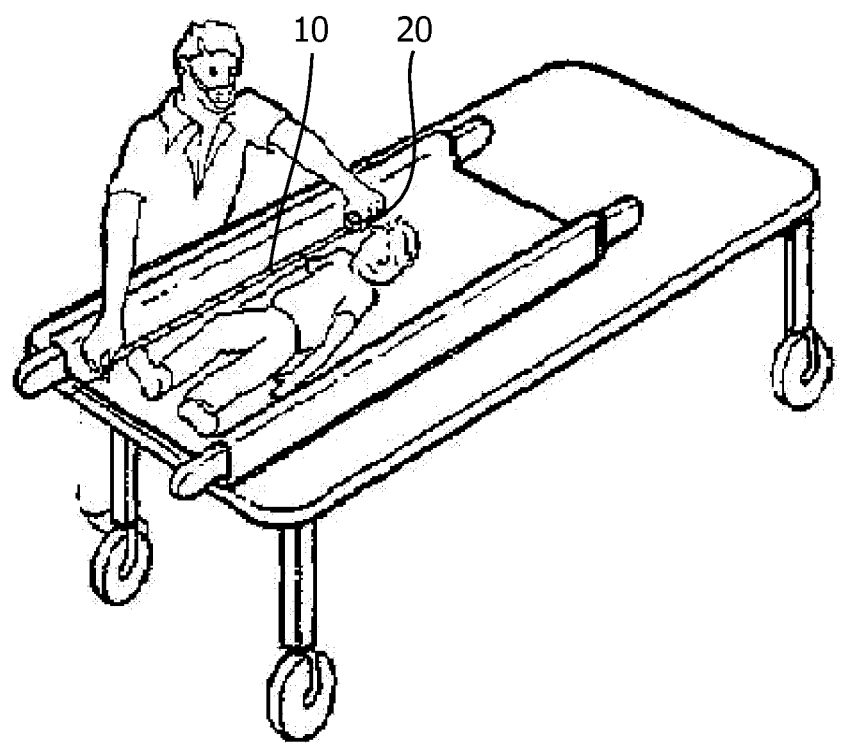
FIG. 1 illustrates a prior art embodiment of a Broselow Tape and its use.
Figure 2A:
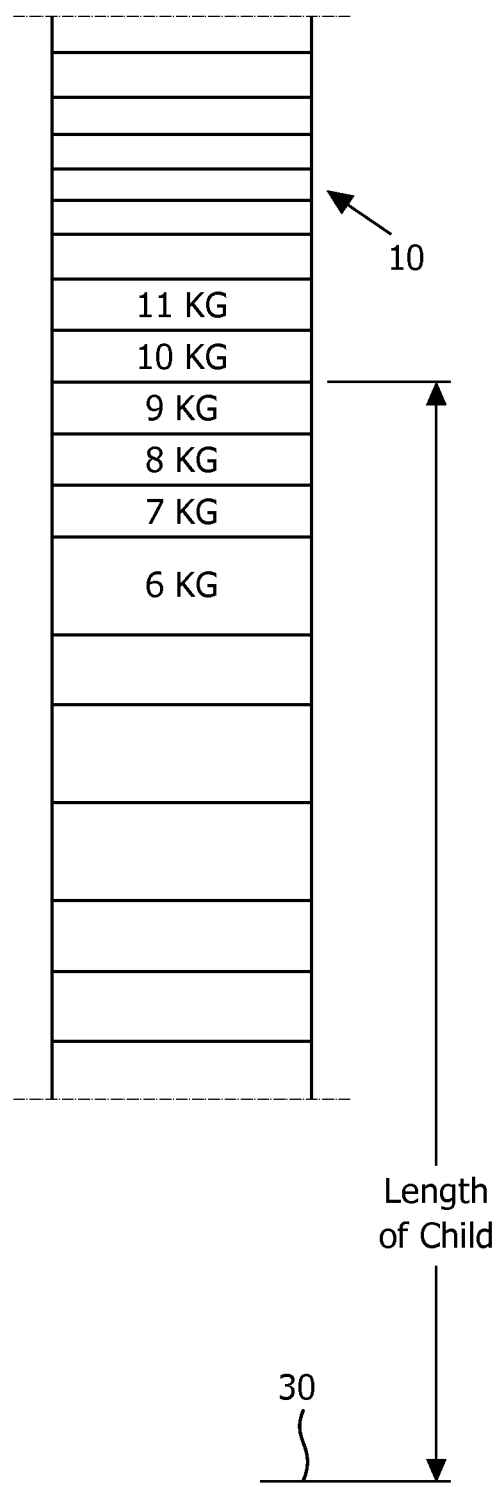
Figure 3:
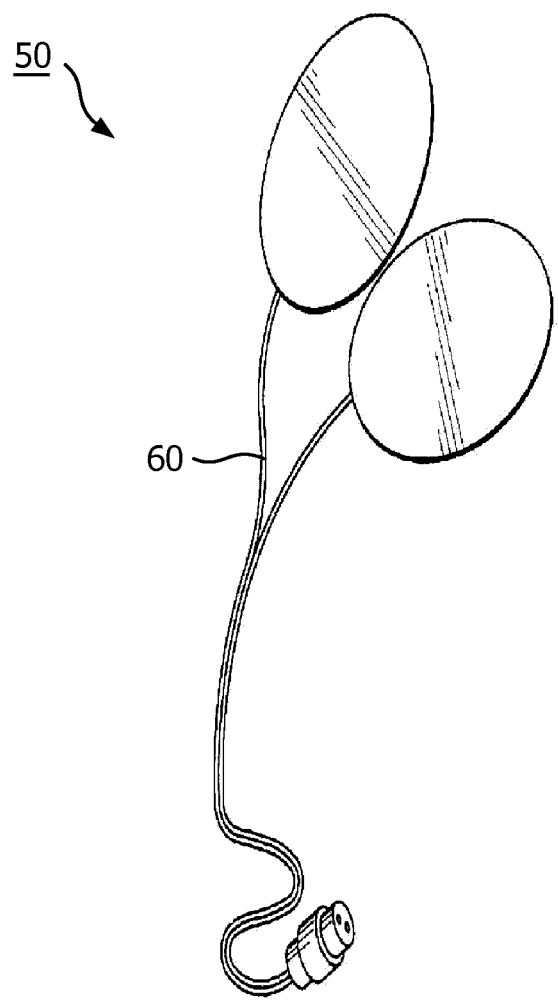
FIG. 3 illustrates one prior art embodiment of an electrode set for use with a cardiac monitor/defibrillator.

Affixed within each location zone 220 is a set of medical guidance instructions 210 which correspond to the patient characteristic for that zone. An example of one set of medical guidance instructions 210 is illustrated on FIG. 2B. There, each zone lists the estimated patient weight for that patient length, followed by appropriate dosages for that patient weight. As can be seen, dosage recommendations include both drug amounts and defibrillation energy amounts. This particular set of instructions corresponds with the Broselow Pediatric Emergency Tape instructions. By integrating these instructions into the electrode lead set, it is assured that the instructions are always present at a pediatric emergency. This helps emergency personnel quickly identify what is needed to save a pediatric patient's life.

Of course, the invention's usefulness is enhanced when the medical guidance instructions are particular to the length measurement. Thus, FIG. 4 also shows a second location zone 240 at a second distance from the index mark 150. The second location zone contains a second set of medical guidance instructions 230. The second location zone 240 is preferably colored differently than the location zone 220.

Figure 5:
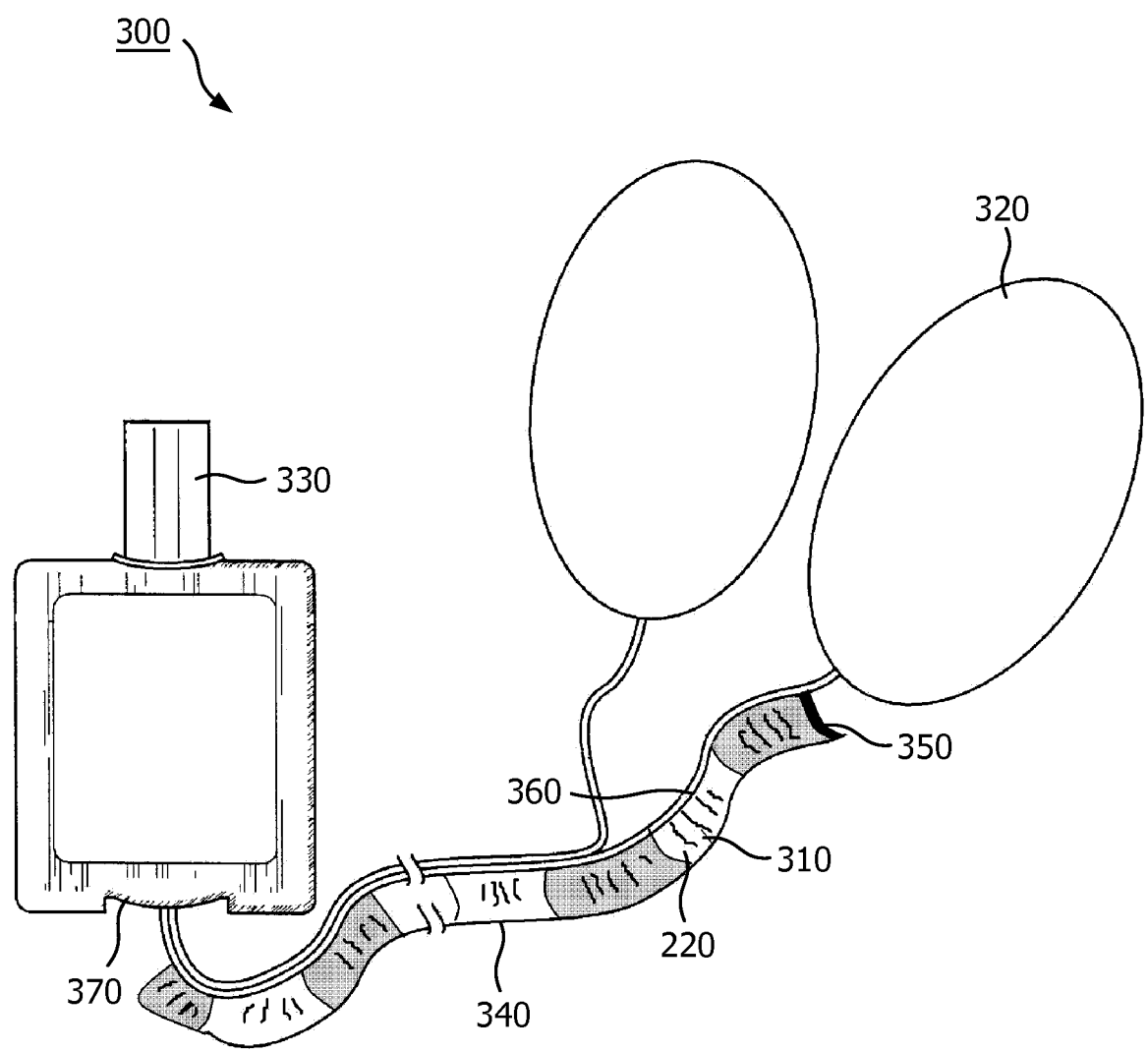
FIG. 5 illustrates an alternate embodiment of the pediatric electrode lead set integrating medical guidance instructions.

FIG. 5 illustrates an alternate embodiment of the present invention, which is an electrode lead set 300 for use exclusively with pediatric patients. Like the afore-described cardiac electrode lead 100, electrode lead set 300 includes one or more adhesive skin electrodes 320, a connector 330 for connecting to a defibrillator, and a lead wire 360 connecting connector 330 to the electrode 320. This alternate electrode embodiment, however, is customized for use with an automatic external defibrillator, or AED. The AED automatically assesses a patient's ECG through the attached skin electrodes 320 and delivers therapy, if appropriate, via the same electrodes 320. But because an AED cannot automatically detect whether the patient is adult or pediatric, special electrode sets must be deployed for use with the pediatric patient. To that end, a defibrillation energy attenuator 370 is disposed within the pediatric electrode lead set 300 which reduces the energy delivered from the AED to the patient.

FIG. 5 further illustrates an instruction placard 340, similar to instruction placard 140, which is attached to lead wire 360. Instruction placard 340 similarly includes medical guidance instructions 310 disposed at a location zone 220 that is offset from an index mark 350. This particular embodiment is advantageous in that only the infrequently-used pediatric electrode lead set 300 must include the instruction placard 340. The instruction placard is unnecessary for use in other, not shown, adult electrode lead sets which are suitable for use with the AED. Thus, expense and clutter are reduced for adult cardiac rescues.

Figure 6A:
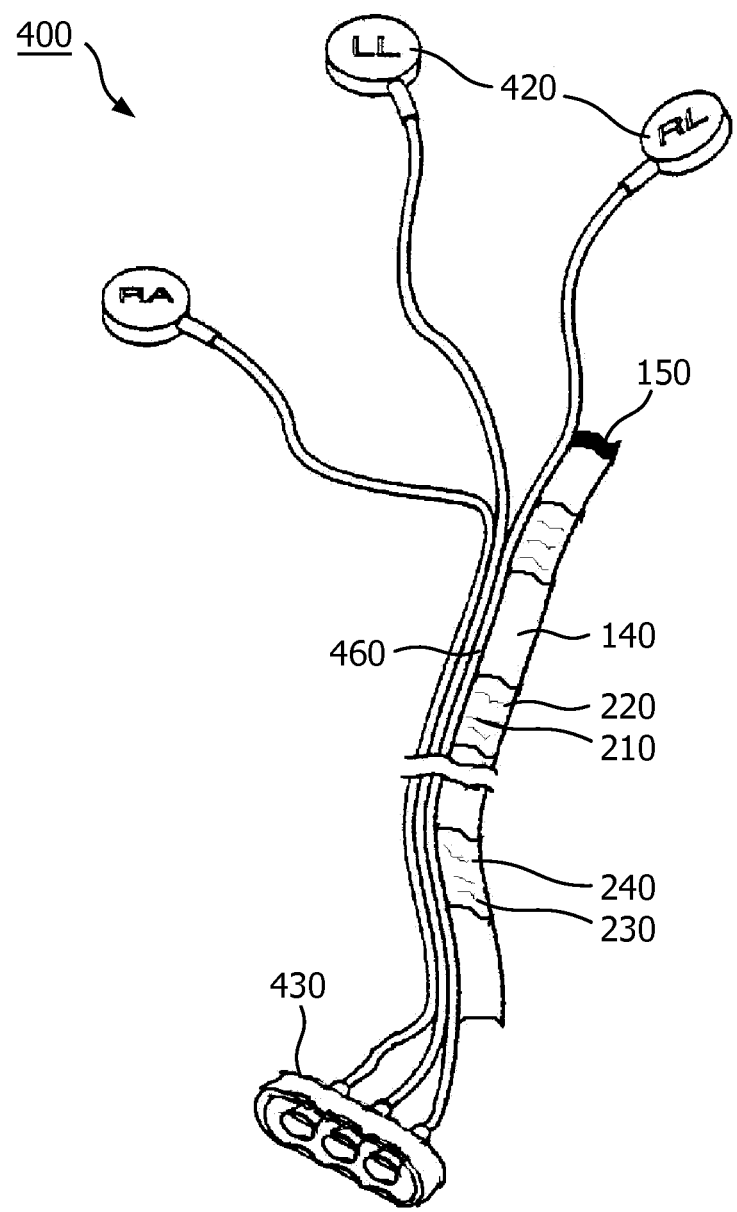
FIG. 6A illustrates an alternate embodiment of an ECG monitoring lead set with integrated medical guidance instructions.

FIG. 6A illustrates an alternate embodiment of the invention wherein the instruction placard 140 is integrated with an ECG monitoring cable 400. The ECG monitoring cable 400 includes one or more ECG skin electrode connectors 420 which are in turn connected to adhesive ECG skin electrodes, not shown. When adhesively applied to a patient's skin, the ECG skin electrodes detect the patient's cardiac electrical signals. The ECG monitoring cable 400 further includes an ECG cable connector 430 for connecting the cable 400 to the cardiac treatment device.

An ECG lead wire 460 connects each of the electrode connectors 420 to a corresponding pin in the ECG cable connector 430. The lead wire is preferably long enough to accommodate use on various sizes of patients without being so long as to interfere with other aspects of the rescue. Preferably, the lead wire is three to four feet in length, and is covered by a polymeric insulation material.

The instruction placard 140 is disposed similarly to, and may be attached to the ECG lead wire 460 in a similar manner, to that previously described. The instruction placard 140 may thus comprise the aforedescribed index mark 150, medical guidance instruction 210 disposed within a location zone 220, and the second medical guidance instruction 230 disposed within a second location zone 240. Of course, the contents of these features may be modified within the scope of the invention to suit the particular needs raised during use of an ECG monitoring cable with pediatric patients.

Figure 6B:
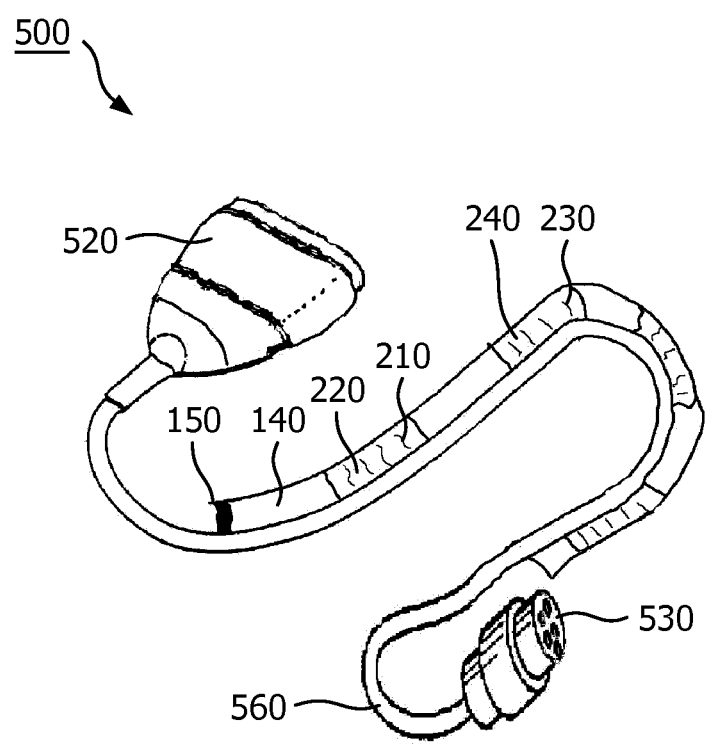
FIG. 6B illustrates an alternate embodiment of a trunk cable which inter-connects and/or adapts a cardiac electrode lead set with a cardiac monitor/defibrillator device.

FIG. 6B illustrates an alternate embodiment of the invention wherein the instruction placard 140 is integrated with a cardiac monitor/defibrillator trunk cable 500. The trunk cable 500 serves to interconnect a patient electrode set, such as cardiac monitor/defibrillator electrode set 50 or cardiac ECG monitoring cable 400, with a device suitable for using the patient electrode set, such as a defibrillator or patient monitor. The trunk cable 500 serves to allow the use of different types and manufactures of patient electrodes with one device, saving time and cost.

Cardiac monitor/defibrillator trunk cable 500 includes at one end a trunk device connector 520 and at the other end a trunk electrode connector 530. A trunk lead wire 560 connects the two one or more ECG skin electrode connectors 420 which are in turn connected to adhesive ECG skin electrodes, not shown. When adhesively applied to a patient's skin, the ECG skin electrodes detect the patient's cardiac electrical signals. The ECG monitoring cable 400 further includes an ECG cable connector 430 for connecting the cable 400 to the cardiac treatment device.

A trunk lead wire 560 in the cardiac monitor/defibrillator trunk cable 500 connects a trunk device connector 520 at one end to a trunk electrode connector 530 at the other end of the lead wire 560. The lead wire is preferably long enough to accommodate use on various sizes of patients without being so long as to interfere with other aspects of the rescue.

Preferably, the lead wire is three to four feet in length, and is covered by a polymeric insulation material.

The instruction placard 140 is disposed similarly to, and may be attached to the trunk lead wire 560 in a similar manner to, that previously described. The instruction placard 140 may thus comprise the aforedescribed index mark 150, medical guidance instruction 210 disposed within a location zone 220, and the second medical guidance instruction 230 disposed within a second location zone 240. Of course, the contents of these features may be modified within the scope of the invention to suit the particular needs raised during use of a trunk cable on pediatric patients.

The inventions of FIGS. 4, 5 and 6 may be used in several ways. As the pediatric rescue begins, the rescuer deploys the particular cardiac treatment device, whether defibrillator, ECG monitor, or AED. The rescuer then deploys a set of electrodes to the pediatric patient's torso, preferably in the anterior/posterior positions. Either before or after applying the adhesive skin electrode to the patient, the rescuer simply extends the lead wire down the length of the patient, with the index mark aligned with the top of the patient's head. The rescuer then refers to the medical guidance instruction at the location zone adjacent to the patient's feet to instantly determine the appropriate therapeutic doses for that particular patient characteristic. Alternatively, the rescuer can align the index mark with the patient's foot and refer to the location zone adjacent to the top of the patient's head. The rescuer can then apply the treatment according to the instruction.

Alternate arrangements of the electrodes and the electrode system of FIGS. 4 through 6 are envisioned which fall within the scope of the claimed invention. For example, the patient characteristic of length can be correlated to patient age. Thus, the patient age may be labeled in the particular location zone. Medical guidance instructions in that location zone may be tailored to the patient age instead of or in addition to weight.

Also, the content of the medical guidance instructions may include other parameters besides the Broselow-type therapies listed in the examples. Such instructions fall within the scope of the claimed invention.

Table of Element Numbers

| Number | Name |
|---|---|
| 10 | Broselow tape - prior art |
| 20 | Pediatric patient |
| 30 | Broselow tape index mark - prior art |
| 40 | Broselow tape instruction - prior art |
| 50 | Cardiac monitor/defibrillator electrode set - prior art |
| 60 | Cardiac monitor/defibrillator electrode lead wire - prior art |
| 100 | Cardiac treatment device electrode lead |
| 120 | Adhesive skin electrode |
| 130 | Connector |
| 160 | Lead wire |
| 140 | Instruction placard |
| 150 | Index mark |
| 210 | Medical guidance instruction |
| 220 | Location zone |
| 230 | Second medical guidance instruction |
| 240 | Second location zone |
| 300 | AED electrode lead set |
| 320 | AED adhesive skin electrode |
| 330 | AED connector |
| 360 | AED lead wire |
| 340 | AED instruction placard |
| 350 | AED index mark |
| 370 | Defibrillation energy attenuator |
| 310 | AED medical guidance instruction |

-continued

Table of Element Numbers

| Number | Name |
|---|---|
| 400 | ECG monitoring cable |
| 420 | ECG skin electrode connector |
| 430 | ECG cable connector |
| 460 | ECG lead wire |
| 500 | Cardiac monitor/defibrillator trunk cable |
| 520 | Trunk device connector |
| 530 | Trunk electrode connector |
| 560 | Trunk lead wire |

What is claimed is:

1. A cardiac treatment device electrode lead comprising:
an adhesive skin electrode;
a connector for connecting the adhesive electrode to a cardiac treatment device;
a lead wire electrically connecting the adhesive electrode to the connector;
a measurement device having a length,
wherein the measurement device comprises a placard forming an integral part of insulation of the lead wire that includes an elongated flap of flexible material fixedly disposed along said length to the lead wire and integrated with pediatric-specific guidance instructions by which a patient characteristic relevant to the cardiac treatment can be obtained; and an index mark disposed at one end of the measurement device,
wherein the patient characteristic relevant to the cardiac treatment is obtained at a location on the measurement device corresponding with a patient length,
further in response to (i) aligning the index mark with one end of the patient, (ii) extending the measurement device and lead wire along the patient length away from the index mark, and (iii) determining the location based on an alignment of an opposite end of the patient with the location on the measurement device away from the index mark,
wherein the lead wire includes a lead wire length greater than said length of the measurement device,
wherein the entire measurement device is fixedly disposed intermediate to and spaced away from opposites ends of the lead wire, and
further wherein the lead wire comprises a length sufficient to enable the entire measurement device, which is intermediate to and spaced away from opposite ends of the lead wire, to be extended down the length of the patient subsequent to applying the adhesive skin electrode to the patient.

2. The cardiac treatment device of claim 1, wherein the measurement device further comprises a medical guidance instruction disposed at a location on the measurement device, the instruction based on a distance from the location to the index mark.

3. The cardiac treatment device of claim 2, further comprising a second medical guidance instruction disposed at a second location on the measurement device, the second instruction based on a second distance from the second location to the index mark.

4. The cardiac treatment device of claim 1, wherein the measurement device is comprises of a flexible polymeric strip that is adhesively disposed along the length of the lead wire.

5. The cardiac treatment device of claim 1, wherein the measurement device is integrally molded to the lead wire.

6. The cardiac treatment device of claim 2, wherein the distance correlates approximately to a measured length of a patient, and further wherein the medical guidance instruction comprises a therapeutic dosage recommendation based on the measured length of the patient.

7. The cardiac treatment device of claim 6, wherein the distance correlates to an age of a patient, and further wherein the medical guidance instruction comprises therapeutic dosage recommendations based upon the age of the patient.

8. The cardiac treatment device of claim 2, wherein the measurement device is color-coded, the color-coding based on a distance from the location to the index mark.

9. The cardiac treatment device of claim 2, wherein the medical guidance instruction is a Broselow guide.

10. The cardiac treatment device electrode lead of claim 1, wherein the lead wire is one selected from the group consisting of a defibrillator electrode lead wire, an ECG lead wire, and a trunk cable lead wire.

11. The cardiac treatment device electrode lead of claim 1, wherein the adhesive skin electrode is a defibrillation electrode and the treatment device is a defibrillator.

12. The cardiac treatment device electrode lead of claim 1, wherein the adhesive skin electrode is a monitoring electrode and the treatment device is a cardiac monitor.

13. A method of providing medical treatment to a patient comprising the steps of:
providing a cardiac treatment device electrode lead having a lead wire with a measurement device having a length,
wherein the measurement device comprises a placard forming an integral part of insulation of the lead wire that includes an elongated flap of flexible material fixedly disposed along said length to the lead wire and integrated with pediatric-specific guidance instructions by which a patient characteristic relevant to the cardiac treatment can be obtained,
wherein the measurement device further comprises an index mark disposed at one end of the measurement device,
wherein the patient characteristic relevant to the cardiac treatment is obtained at a location on the measurement device corresponding with a patient length,
further in response to (i) aligning the index mark with one end of the patient, (ii) extending the measurement device and lead wire along the patient length away from the index mark, and (iii) determining the location based on an alignment of an opposite end of the patient with the location on the measurement device away from the index mark,
wherein the lead wire includes a lead wire length greater than said length of the measurement device,
wherein the entire measurement device is fixedly disposed intermediate to and spaced away from opposites ends of the lead wire, and
further wherein the lead wire comprises a length sufficient to enable the entire measurement device, which is intermediate to and spaced away from opposite ends of the lead wire, to be extended down the length of the patient subsequent to applying the adhesive skin electrode to the patient;
deploying the electrode lead to a patient; aligning the index mark at one end of the patient;
extending the lead wire from the one end of the patient to a second end of the patient to obtain a patient characteristic with the measurement device;
obtaining a medical guidance instruction printed on the measurement device and located at a location on the measurement device adjacent to the second end of the patient, the guidance instruction being tailored to the patient characteristic; and
applying medical treatment to the patient according to the medical guidance instruction.

14. The method of claim 13, further comprising the step of electrically connecting the electrode lead to a cardiac treatment device.

15. The method of claim 14, wherein the step of electrically connecting occurs prior to the steps of deploying, aligning, extending and obtaining.

16. The method of claim 14, wherein the step of electrically connecting occurs after the steps of deploying, aligning, extending and obtaining.

17. The method of claim 14, wherein the medical guidance instruction comprises instructions for therapeutic dosage that is appropriate for a patient having the patient characteristic.

18. The method of claim 17, wherein the patient characteristic is length.

19. The method of claim 18, wherein the patient length characteristic is further characterized by a patient weight.

20. The method of claim 18, wherein the patient length characteristic is further characterized by a patient age.

* * * * *